United States Patent
Suzuki et al.

[11] Patent Number: 6,165,160
[45] Date of Patent: Dec. 26, 2000

[54] DISPOSABLE DIAPER

[75] Inventors: Naomi Suzuki; Yoshitaka Mishima, both of Kagawa-ken, Japan

[73] Assignee: Uni-Charm Corporation, Ehime-ken, Japan

[21] Appl. No.: 09/395,520

[22] Filed: Sep. 14, 1999

[30] Foreign Application Priority Data

Sep. 14, 1998 [JP] Japan .................................. 10-260571

[51] Int. Cl.[7] .................................................. A61F 13/15
[52] U.S. Cl. .............................. 604/385.201; 604/385.01; 604/385.04; 604/385.28
[58] Field of Search ........................ 604/385.01, 385.04, 604/385.201, 385.28, 385.21

[56] References Cited

U.S. PATENT DOCUMENTS

| | | | |
|---|---|---|---|
| 3,710,797 | 1/1973 | Marsan | 128/284 |
| 3,877,432 | 4/1975 | Gellert | 128/287 |
| 3,963,029 | 6/1976 | Brooks | 128/287 |
| 4,300,563 | 11/1981 | Brookfield | 128/287 |
| 4,676,787 | 6/1987 | Sergeant | 604/384 |
| 4,781,712 | 11/1988 | Barabino et al. | 604/385.1 |
| 5,454,803 | 10/1995 | Sageser et al. | 604/385.2 |
| 5,569,228 | 10/1996 | Byrd et al. | 604/385.1 |
| 5,706,950 | 1/1998 | Houghton et al. | 206/581 |
| 5,864,890 | 2/1999 | Niedermeyer | 2/403 |

FOREIGN PATENT DOCUMENTS 58-13704   1/1983   Japan .

Primary Examiner—John G. Weiss
Assistant Examiner—Paul Shanoski
Attorney, Agent, or Firm—Baker & Daniels

[57] ABSTRACT

A diaper is folded along a first folding guide line extending in a transverse direction of the diaper so as to divide its longitudinal dimension in two toward the outer surface of a backsheet, then along a pair of second folding guide lines extending in parallel to each other in the transverse direction of the diaper and lying between the first folding guide line and longitudinally outer ends of front and rear waist regions toward an outer surface of a topsheet and finally along a pair of third folding guide lines extending in parallel to each other in a longitudinal direction of the diaper along transversely opposite side edges of an absorbent core toward an outer surface of the backsheet in any one of the front and rear waist regions.

4 Claims, 4 Drawing Sheets

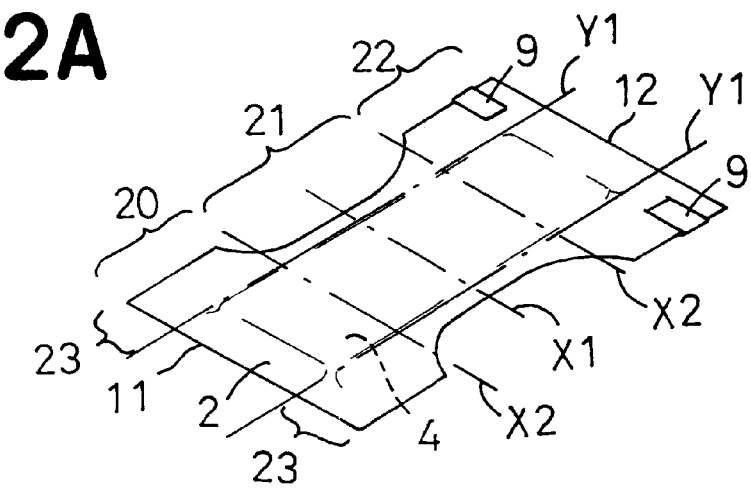
FIG.2A
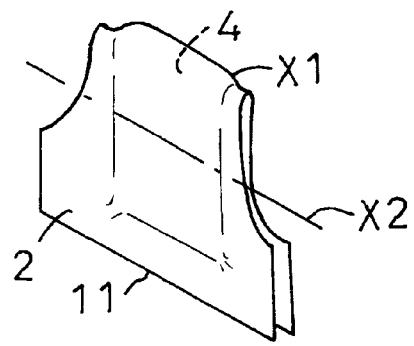
FIG.2B
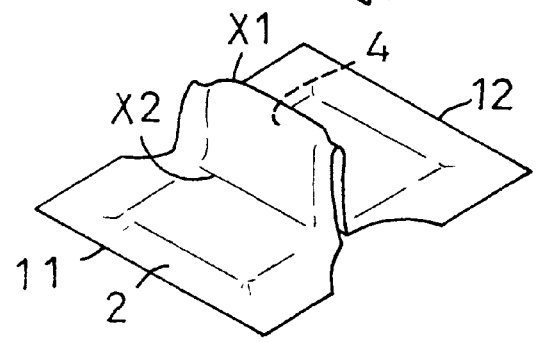
FIG.2C
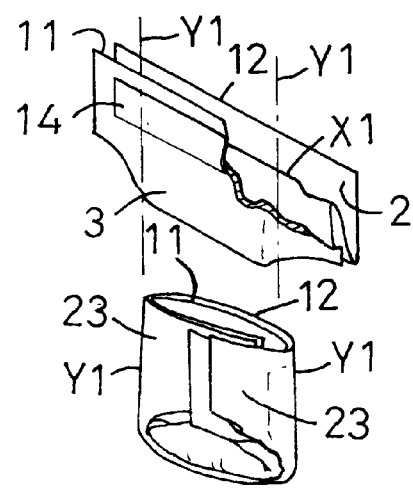
FIG.2D
FIG.2E

DISPOSABLE DIAPER

BACKGROUND OF THE INVENTION

This invention relates to an open type disposable diaper for absorption and containment of body wastes.

Japanese Patent Application Disclosure Gazette (Kokai) No. Sho58-13704 describes a disposable diaper comprising a liquid-pervious topsheet, a liquid-impervious backsheet, a liquid-absorbent core disposed between these two sheets, and a pair of side flaps extending transversely outward from transversely opposite side edges of the absorbent core. The side flaps are provided with elastic members longitudinally extending along the respective side edges of the absorbent core between the topsheet and the backsheet and bonded with under tension between the topsheet and the backsheet. The side flaps are folded back toward the topsheet above an area of the absorbent core along a pair of folding lines which extend in parallel to each other longitudinally of the diaper along the side edges of the absorbent core, respectively, so that the side flaps may be placed upon the topsheet above the area of the absorbent core. Then, along a pair of folding lines which extend in parallel to each other transversely of the diaper and substantially trisect a longitudinal dimension of the diaper, the diaper is folded one upon another in three layers with the topsheet inside.

In the case of the diaper described in the Japanese Patent Application Disclosure Gazette (Kokai) No. Sho58-13704, the side flaps are apt to be formed with permanent folds along the respective folding lines as a long period elapses after the diaper was folded since the side flaps are held between sections of the folded basic structure of the diaper. Each of the elastic members secured to the side flaps should be inevitably stretched on the folding line by a length corresponding to a thickness of the diaper basic structure as the diaper is folded. Under a contractile force of the elastic member thus stretched, the topsheet as well as the absorbent core are apt to be creased. Furthermore, in order to unfold the diaper and to put it on a wearer's body, this diaper inconveniently requires two steps of operation, i.e., the diaper folded in three layers must be opened longitudinally of the diaper and then the side flaps having permanent folds must be open transversely of the diaper.

SUMMARY OF THE INVENTION

It is an object of this invention to provide a disposable diaper adapted to be folded in such a manner that a topsheet as well as an absorbent core can be kept substantially free from being creased and the diaper can be opened with a single step of operation.

According to this invention, there is an open type disposable diaper having a front waist region, a rear waist region and a crotch region extending between the front and rear waist regions, the diaper including a liquid-pervious topsheet, a liquid-impervious backsheet, a liquid-absorbent core disposed between the topsheet and the backsheet and a pair of side flaps extending outward in a transverse direction from transversely opposite side edges of the absorbent core.

The diaper of the present invention has a first folding guide line extending in a transverse direction of the diaper so as to bisect a longitudinal dimension of the diaper, a pair of second folding guide lines extending in parallel to each other in the transverse direction of the diaper between the first folding guide line and respective outer ends of the front and rear waist regions and a pair of third folding guide lines extending in parallel to each other in a longitudinal direction of the diaper along the side edges of the absorbent core; and the diaper is folded in the longitudinal direction thereof along the first folding guide line toward an outer surface of the backsheet, then along the pair of second folding guide lines toward an outer surface of the topsheet and finally the pair of side flaps are folded along the pair of third folding guide lines toward the outer surface of the backsheet in any one of the front and rear waist regions.

According to one embodiment of this invention, each of first dimensions defined in the longitudinal direction between the first folding guide line and the pair of second folding guide lines, respectively, is smaller than each of second dimensions defined in the longitudinal direction between the pair of second folding guide lines and the outer ends of the front and rear waist regions lying adjacent respective the outer ends.

According to another embodiment of this invention, the pair of first dimensions are equal to each other and the pair of second dimensions are equal to each other.

According to still another embodiment of this invention, a dimension defined in the transverse direction between the pair of third folding guide lines is larger than a dimension defined in the transverse direction between the side edges of the absorbent core and a pair of dimensions defined in the transverse direction between the third folding guide lines and outer side edges of the side flaps lying adjacent respective the third folding guide lines are equal to each other.

BRIEF DESCRIPTION OF THE DRAWINGS

FIG. 2 is a perspective view stepwise illustrating how to fold the diaper;

DETAILED DESCRIPTION OF THE PREFERRED EMBODIMENTS

Details of an open type disposable diaper according to this invention will be more fully understood from the description given hereunder with reference to the accompanying drawings.

Figure 1:
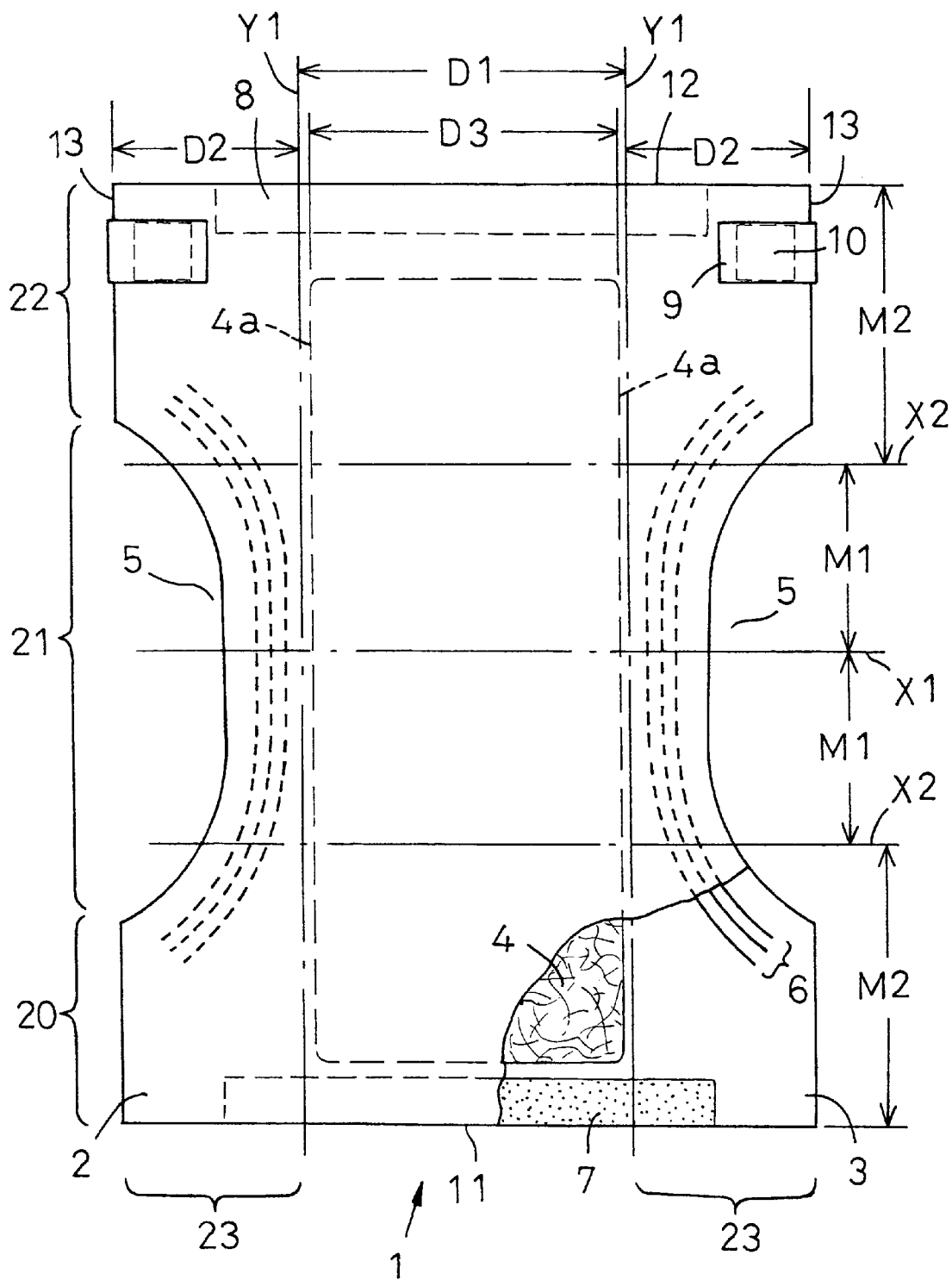
FIG. 1 is a plan view showing one embodiment of a partially cut away disposable diaper according to this invention.

FIG. 1 is a plan view showing a partially cut away disposable diaper in its unfolded state and FIG. 2 is a perspective view stepwise illustrating how to fold the diaper 1. A disposable diaper 1 has a front waist region 20, a rear waist region 22 and the crotch region 21 extending between these front and rear waist regions 20, 22. The diaper 1 includes a liquid-pervious topsheet 2, a liquid-impervious backsheet 3, a liquid-absorbent core 4 disposed between these two sheets 2, 3 and bonded between an inner surface of these two sheets 2, 3. Portions of the topsheet 2 and the backsheet 3 extending outward beyond transversely opposite side edges 4a of the absorbent core 4 form a pair of side flaps 23.

The diaper 1 has a first folding guide line X1 extending transversely of the diaper 1 so as to bisecting a longitudinal dimension thereof; a pair of second folding guide lines X2 extending in parallel to each other transversely of the diaper 1 and lying between the first folding guide line X1 and longitudinal opposite ends 11, 12 of the diaper 1, i.e., outer ends of the front and rear waist regions 20, 22, respectively; and a pair of third folding guide lines Y1 extending in parallel to each other longitudinally of the diaper 1 and lying immediately outside the respective side edges of the absorbent core 4.

A first dimension M1 of the diaper 1 as defined longitudinally thereof between the first folding guide line X1 and each of the second folding guide lines X2 is smaller than a second dimension M2 of the diaper 1 as defined longitudinally thereof between each of the second folding guide lines X2 and the adjacent outer end 11 or 12 of the front or rear waist region 20 or 22. The pair of the first dimensions M1 are equal to each other and the pair of the second dimensions M2 are also equal to each other. A dimension D of the diaper 1 as defined transversely thereof between the pair of the third folding guide lines Y1 is larger than a transverse dimension D3 of the diaper 1 as defined between the side edges 4a of the absorbent core 4. A pair of third dimensions D2 of the diaper 1 as defined transversely thereof between the respective third folding guide lines Y1 and the adjacent side edges 13 of the respective side flaps 23 are equal to each other.

In the crotch region 22, each side flap 23 is formed with a cutout 5 curved inwardly of the diaper 1 and three elastic members 6 are arranged longitudinally of the diaper 1 so as to extend along the cutout 5 between the topsheet 2 and the backsheet 3. These elastic members 6 are secured under tension to the inner surface of at least one of said topsheet 2 and the backsheet 3.

Along the longitudinally opposite ends 11, 12 of the diaper 1, i.e., the outer ends of the front and rear waist regions 20, 22, respectively, film-like elastic members 7, 8 extend between the topsheet 2 and the backsheet 3 transversely of the diaper 1. These film-like elastic members 7, 8 are secured under tension to the inner surface of at least one of the topsheet 2 and the backsheet 3. Transversely opposite ends of the rear waist region 22 are provided with a pair of tape fasteners 9, respectively. These tape fasteners 9 transversely extend from the respective side edges of the rear waist region 22 inwardly of the diaper 1 and have their proximal ends disposed between and inseparably secured to the topsheet 2 and the backsheet 3. The tape fasteners 9 have their free ends coated with adhesive agent 10. A strip of target tape 14 is bonded to an outer surface of the front waist region 20 so that the strip of target tape 14 may serve as anchoring zone 12 for the tape fasteners 9. The tape fasteners 9 may be anchored on the strip of target tape 14 by means of adhesive agent 10 applied on an inner surfaces of the respective tape fasteners 9 to form a waist-opening and a pair of leg-openings (not shown).

The diaper 1 can be folded by following steps (A)–(E) as illustrated in FIG. 2. The diaper 1 is folded along the first folding guide line X1 from its flattened state as illustrated in the step (A) of FIG. 2 so that the diaper 1 is folded in two with the outer surface sections of the backsheet 3 thus folded being opposed to each other and the outer ends 11, 12 of the front and rear waist regions 20, 22 are placed upon each other as illustrated in the step (b) of FIG. 2. The sections of the diaper 1 thus folded in two which extend between the respective second folding guide lines X2 and the adjacent the outer ends 11, 12 of the front and rear waist regions 20, 22, respectively, are then folded along the second folding guide lines X2 so that the topsheet may have its outer surface sections opposed to and placed upon each other as illustrated in the step (C) of FIG. 2. In this manner, the diaper 1 is folded in W-shape so that the sections of the diaper 1 extending from the first folding guide line X1 to the second folding guide lines X2 may be placed upon the sections of the diaper 1 extending from the second folding guide lines X2 to the outer ends 11, 12 of the front and rear waist regions 20, 22, respectively. As will be apparent from (D) of FIG. 2, the sections of the diaper 1 extending between the first folding guide line X1 and the second folding guide lines X2 are not exposed outward beyond the respective outer ends 11, 12 of the front and rear waist regions 20, 22 because the first dimensions M1 of the diaper 1 are smaller than the second dimensions M2 of the diaper 1. Therefore, it is not apprehended that the topsheet 2 might be soiled with body wastes.

The side flaps 23 of the diaper 1 folded in a W-shape are folded along the third folding guide lines Y1 in the front waist region 20 as illustrated by (E) of FIG. 2 so that the outer surface sections of the backsheet 3 are placed upon each other. It is also possible to fold the side flaps 23 in the rear waist region 22 of the diaper 1. The side flaps 23 are substantially free from any permanent folds since they are not held between folded sections of the diaper basic structure. The absorbent core 4 is also free from any permanent folds which might be caused by the third folding guide lines Y1. This for the reason that the third folding guide lines Y1 lie immediately outside the respective side edges 4a of the absorbent core 4 and said core 4 is never folded along the third folding guide lines Y1.

Figure 3:
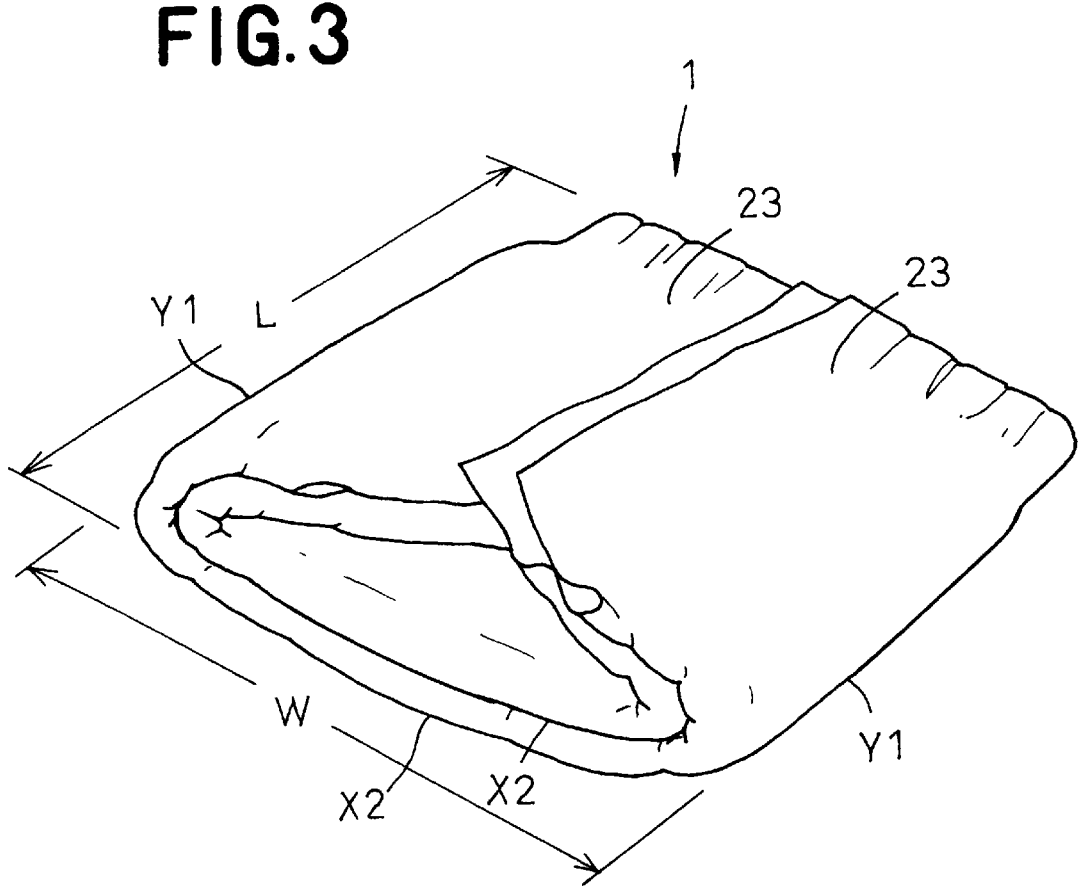
FIG. 3 is a perspective view showing the diaper in its folded state.

FIG. 3 is a perspective view showing the diaper 1 in its folded state. Regarding the manner in which the diaper is folded, the diaper 1 known under the Trademark "MOONY M" having a longitudinal dimension of 45.0 cm and a transverse dimension of 31.5 cm in its unfolded state was used for the purpose of comparative determination of effects obtained by folding the same diaper 1 in thirds longitudinally thereof in the conventional manner, on one hand, and in the manner according to this invention, on the other hand. Folding the diaper 1 in the conventional manner resulted in a longitudinal dimension L of 15.5 cm, a transverse dimension W of 12.7 cm and a surface area of 196.85 cm$^2$. On the other hand, folding the same diaper 1 in the manner according to this invention resulted in a longitudinal dimension L of 11.0 cm, a transverse dimension W of 14.5 cm and a surface area of 159.5 cm. It was found from this comparison that the manner of folding according to this invention allows the diaper 1 to be more compactly folded than the case adopting the conventional manner of folding. To unfold the diaper 1 from its folded state as shown in FIG. 3, the diaper 1 may be held by the fingers in the vicinity of the outer ends 11, 12 of the front and rear waist regions 20, 22, respectively, and then the diaper 1 may be developed longitudinally thereof.

Figure 4:
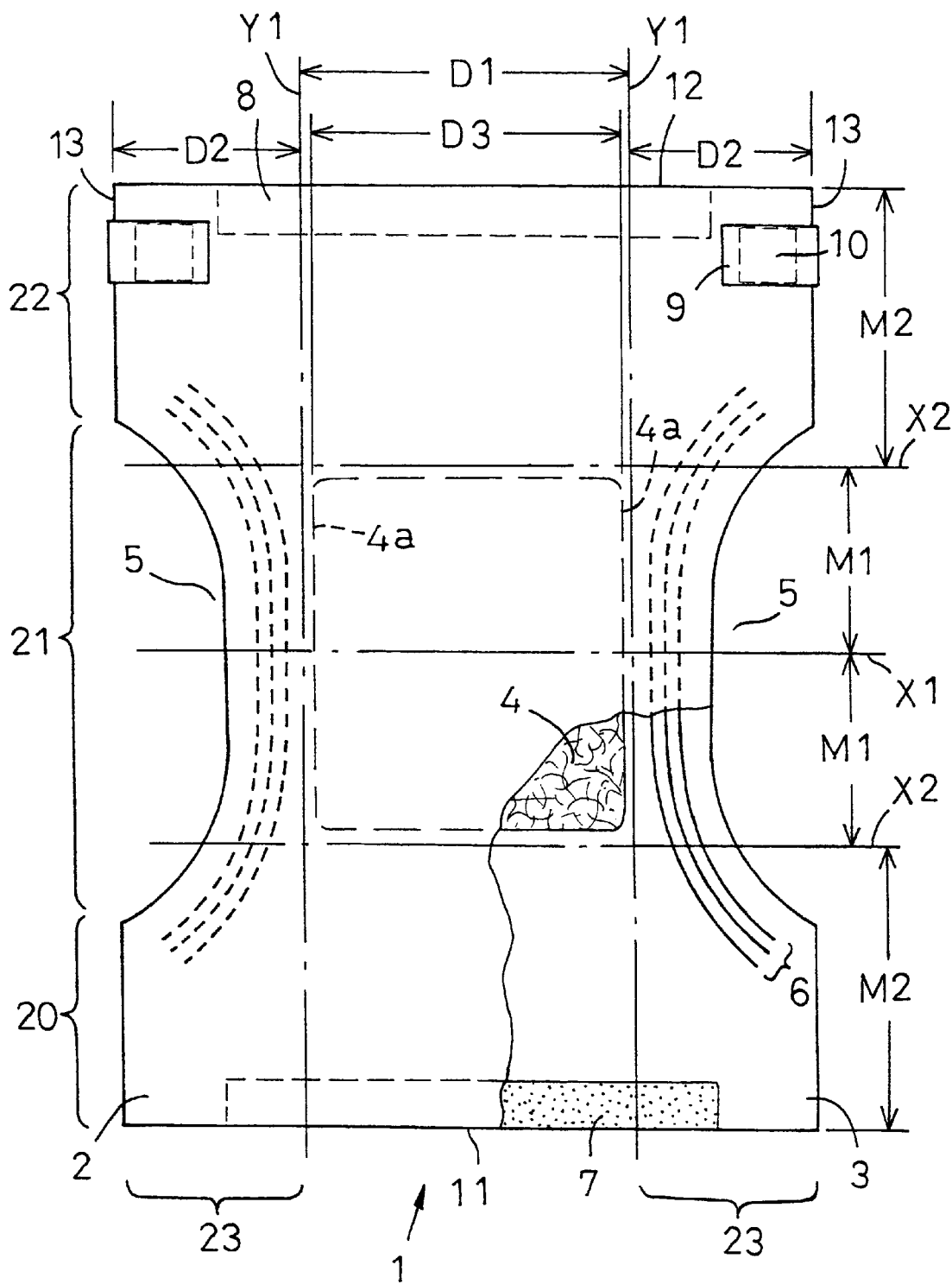
FIG. 4 is a view similar to FIG. 1 but showing another embodiment of the diaper according to this invention.

FIG. 4 is a view similar to FIG. 1 but showing the diaper 1 according to an alternative embodiment of this invention as partially broken away. As will be apparent from FIG. 4, the absorbent core 4 occupies a zone extending from the first folding guide line X1 to the respective second folding guide lines X2, i.e., a total zone defined between the pair of second folding guide lines X2. The absorbent core 4 is not present in zones of the diaper 1 defined between the respective outer ends 11, 12 of the front and rear waist regions 20, 22 and the second folding guide lines X2, X2 adjacent the waist regions 20, 22. Therefore, the diaper 1 may be longitudinally folded along the first folding guide line X1 and then along the respective second folding guide lines X2 to reduce a thickness of the diaper 1 in its folded state by a thickness of the absorbent core 4. The core 4 may occupy, in addition to the zone defined between the pair of second folding guide lines X2, one of zones respectively defined between the outer end 11 of the front waist region 20 and the second folding guide line X2 lying adjacent the outer end 11 and between the outer end 12 of the rear waist region 22 and the second folding guide line X2 lying adjacent the outer end 12.

If the basic structure of the diaper 1 is folded after the side flaps 23 have been folded back onto the absorbent core 4, the elastic members 6 secured to the side flaps 23 would be longitudinally stretched by a thickness of the basic structure of the diaper 1 on the lines along which the basic structure of the diaper 1 is folded. Consequently, the topsheet 2 as well as the absorbent core 4 would often be creased under the contractile force of the elastic members 6. With the diaper 1 according to this invention, on the contrary, it is not apprehended that the elastic members 6 might be longitudinally stretched as the basic structure of the diaper 1 is folded because the side flaps 23 are not held between the folded basic structure of the diaper 1. Accordingly, there is no apprehension that the topsheet 2 as well as the absorbent core 4 might be creased under the contractile effect of the elastic members 6.

It is also possible without departing the scope of this invention to form the side flaps 23 by combining a liquid-resistant sheet transversely extending outward from the side edges 4a of the absorbent core 4 and the backsheet 3 transversely extending outward beyond the side edges 4a of the absorbent core 4. The liquid-resistant sheet may be bonded to the upper surface of the topsheet 2 to prevent moisture contained in excretion from soaking into the side flaps 23.

A hydrophobic nonwoven fabric treated with suitable hydrophiling agent or a hydrophilic nonwoven fabric obtained by kneading suitable hydrophiling agent into fibers is used as stock material for the topsheet 2. Instead of such nonwoven fabric, an apertured thermoplastic synthetic resin film also may be useful as stock material for the topsheet 2.

Stock materials for the backsheet 3 and the liquid-resistant sheet may be selected from a group consisting of a synthetic resin film, a laminated sheet comprising a synthetic resin film and a hydrophobic nonwoven fabric, etc. The absorbent core 4 is a mixture of fluff pulp and super-absorptive polymer particles which is compressed to a desired thickness and entirely covered with a water-pervious sheet such as tissue paper. To bond these members together, adhesive agent such as hot melt adhesive agent or glue may be used and, for the heat-sealable members, the heat-sealing technique may be also used.

This invention is applicable also to a diaper further including a second pair of side flaps bonded to the upper surface of the side flaps 23 and provided along free edges of these second side flaps with elastic members secured thereto under tension so that these second side flaps may rise on the diaper 1 as the elastic members contract.

With the disposable diaper according to this invention, the diaper can be easily unfolded merely by longitudinally developing the folded diaper with the fingers holding the diaper in the vicinity of the respective outer ends of the front and rear waist regions. The basic structure of the diaper is folded with the side flaps lying outside the transversely opposite side edges of the absorbent core so that the elastic members bonded to the respective side flaps may be free from undesirable stretch due to a thickness of the diaper basic structure and, therefore, the topsheet as well as the absorbent core are substantially free from being creased under the contractile force of these elastic members.

What is claimed is:

1. A disposable diaper comprising:

a front waist region;

a rear waist region;

a crotch region between said front waist region and said rear waist region;

a liquid-pervious topsheet;

a liquid-impervious backsheet;

a liquid-absorbent core disposed between said liquid-pervious topsheet and said liquid-impervious backsheet; and a pair of side flaps extending outward in a transverse direction from transversely opposite side edges of said liquid-absorbent core, said diaper having a first folding guide line extending in a transverse direction of said diaper which bisects a longitudinal dimension of said diaper, a pair of second folding guide lines extending in parallel to each other in said transverse direction of said diaper between said first folding guide line and respective outer ends of said front and rear waist regions and a pair of third folding guide lines extending in parallel to each other in a longitudinal direction of said diaper along said side edges of said absorbent core, said diaper being folded in said longitudinal direction thereof along said first folding guide line toward an outer surface of said liquid-impervious backsheet, then along said pair of second folding guide lines toward an outer surface of said liquid-pervious topsheet and finally said pair of side flaps are folded along said pair of third folding guide lines toward the outer surface of said liquid-impervious backsheet in one of said front and rear waist regions.

2. The diaper according to claim 1, wherein each of first dimensions defined in said longitudinal direction between said first folding guide line and said pair of second folding guide lines, respectively, is smaller than each of second dimensions defined in said longitudinal direction betweem said pair of second folding guide lines and said outer ends of said front and rear waist regions lying adjacent respective said outer ends.

3. The diaper according to claim 2, wherein said pair of first dimensions are equal to each other and said pair of second dimensions are equal to each other.

4. The diaper according to claim 1, wherein a dimension defined in said transverse direction between said pair of third folding guide lines is larger than a dimension defined in said transverse direction between said side edges of said absorbent core and outer most side edges of said side flaps.

* * * * *